United States Patent [19]

Dellaria et al.

[11] Patent Number: 5,446,055

[45] Date of Patent: Aug. 29, 1995

[54] POLYETHER NAPHTHALENIC LIGNAN LACTONES AS INHIBITORS OF 5-LIPOXYGENASE

[75] Inventors: Joseph F. Dellaria, Lindenhurst; James D. Ratajczyk, Waukegan; Clint D. W. Brooks, Libertyville; Anwer Basha, Lake Forest, all of Ill.

[73] Assignee: Abbott Laboratories, Abbott Park, Ill.

[21] Appl. No.: 344,443

[22] Filed: Nov. 23, 1994

[51] Int. Cl.$^6$ .................. A61K 31/44; C07D 307/92
[52] U.S. Cl. ........................ 514/337; 514/439; 514/444; 514/463; 514/468; 514/529; 546/269; 560/56; 549/60; 549/299; 549/451; 549/453
[58] Field of Search ............... 549/60, 299, 451, 453; 546/269; 560/56; 514/337, 444, 463, 468, 439, 529

[56] References Cited

U.S. PATENT DOCUMENTS

| | | | |
|---|---|---|---|
| 3,704,247 | 11/1972 | Munakata | 549/299 |
| 4,897,418 | 1/1990 | Iwasaki et al. | 514/468 |
| 5,210,230 | 5/1993 | Payack | 549/299 |

*Primary Examiner*—C. Warren Ivy
*Assistant Examiner*—Amelia Owens
*Attorney, Agent, or Firm*—Jerry F. Janssen

[57] ABSTRACT

Compounds of formula

Ar is optionally substituted phenyl, furyl, pyridyl, or thienyl; Y is selected from hydrogen, halogen, cyano, alkyl, haloalkyl, alkoxy, and alkoxycarbonyl; L is selected from

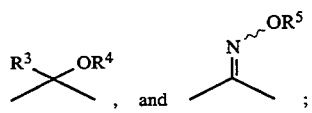 , and ;

and $R^1$ and $R^2$ are alkyl or together define a group of formula

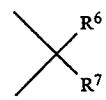

are potent inhibitors of lipoxygenase enzymes and thus inhibit the biosynthesis of leukotrienes. These compounds are useful in the treatment or amelioration of allergic and inflammatory disease states.

11 Claims, No Drawings

POLYETHER NAPHTHALENIC LIGNAN LACTONES AS INHIBITORS OF 5-LIPOXYGENASE

TECHNICAL FIELD

This invention relates to compounds having biological activity to inhibit lipoxygenase enzymes, to pharmaceutical compositions comprising these compounds, and to a medical method of treatment. More particularly, this invention concerns certain 1,2-dialkoxyethyl compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, convening them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to LTA$_4$. This reactive leukotriene intermediate is enzymatically hydrated to LTB$_4$ or conjugated to the tripeptide glutathione to produce LTC$_4$. LTA$_4$ can also be hydrolyzed nonenzymatically to form two isomers of LTB$_4$. Successive proteolytic cleavage steps convert LTC$_4$ to LTD$_4$ and LTE$_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a as number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain polyether naphthalenic lignan lactone compounds which inhibit lipoxygenase enzyme activity and are useful in the treatment of allergic and inflammatory disease states in which leukotrienes play a part.

The present invention provides a compound of formula I

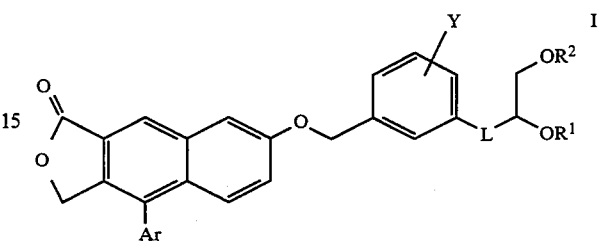

or a pharmaceutically acceptable salt thereof where Ar is selected from (a) phenyl, (b) phenyl substituted with one or more groups selected from halogen, cyano, alkyl of one to four carbon atoms, haloalkyl of one to four carbon atoms, alkoxy of one to six carbon atoms, and alkoxycarbonyl where the alkyl portion is of one to four carbon atoms, (c) furyl, (d) furyl substituted with one or more groups selected from halogen, alkyl of one to four carbon atoms, and alkoxy of one to four carbon atoms, (d) pyridyl, (e) pyridyl substituted with one or more groups selected from halogen, alkyl of one to four carbon atoms, and alkoxy of one to four carbon atoms, (f) thienyl, and (g) thienyl substituted with one or more groups selected from halogen, alkyl of one to four carbon atoms, and alkoxy of one to four carbon atoms.

Y is selected from hydrogen, halogen, cyano, alkyl of one to four carbon atoms, haloalkyl of one to four carbon atoms, alkoxy of one to six carbon atoms, and alkoxycarbonyl wherein the alkyl portion is of one to four carbon atoms.

L is selected from
(a)

where R$^3$ is hydrogen or alkyl of one to four carbon atoms, and R$^4$ is alkyl of one to four carbon atoms, and
(b)

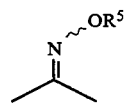

where R$^5$ is hydrogen or alkyl of one to four carbon atoms.

R$^1$ and R$^2$ are alkyl of one to four carbon atoms, or taken together with the oxygen atoms to which they are attached define a group of formula

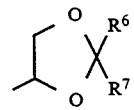

where $R^6$ and $R^7$ are independently selected from hydrogen, alkyl of one to four carbon atoms, alkoxy of one to four carbon atoms, and haloalkyl of one to four carbon atoms and the free valence bond is attached to L in the generic structure I above.

In another embodiment, the present invention provides pharmaceutical compositions which comprise a therapeutically effective amount of compound as defined above in combination with a pharmaceutically acceptable carrier.

In yet another embodiment, the present invention provides a method of inhibiting leukotriene biosynthesis in a mammal in need of such treatment comprising administering to a mammal in need of such treatment a therapeutically effective amount of a compound as defined above.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in J. Pharmaceutical Sciences, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, as dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmirate, pamoate, pectinate, persulfate, 3-phenylpropionate, phosphate, picrate, pivalate, propionate, stearate, succinate, sulfate, tanrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Certain compounds of this invention may exist in either cis or trans or E or Z isomers with respect to the oxime geometry and in addition to stereoisomeric forms by virtue of the presence of one or more chiral centers. The present invention contemplates all such geometric and stereoisomers, including R- and S-enantiomers, diastereomers, and cis/trans or E/Z mixtures thereof as falling within the scope of the invention. If a particular enantiomer is desired, it may be prepared by asymmetric synthesis or by derivatization with a chiral auxiliary and the resulting diastereomeric mixture is separated and the auxiliary group cleaved to provide the pure desired enantiomers.

Preferred Embodiments

Compounds contemplated as falling within the scope of the present invention include, but are not limited to:

O-methylE- and Z-(4"S)-7-[(3'-((2",2"-dimethyl-1",3"-dioxolan-4"-yl)oximinomethyl)phenyl)oxymethylene]-4-(4-fluorophenyl)naptho[2,3-c]-furan-1(3H)-one, O-methylE- and Z-(4"S)-7-[(3'-((2",2"-dimethyl-1",3"-dioxolan-4"-yl)oximinomethyl)phenyl)oxymethylene]-4-phenylnaptho[2,3-c]furan-1(3H)-one, O-methylE- and Z-(4"S)-7-[(3'-((2",2"-dimethyl-1",3"-dioxolan-4"-yl)oximinomethyl)phenyl)oxymethylene]-4-(4-chlorophenyl)naptho[2,3-c]furan-1(3H)-one, O-methylE- and Z-(4"S)-7-[(3'-((2",2"-dimethyl-1",3"-dioxolan-4"-yl)oximinmethyl)phenyl)oxymethylene]-4-(4-methoxyphenyl)naptho[2,3-c]furan-1(3H)-one, O-methylE- and Z-(4"S)-7-[(3"-((2",2"-dimethyl-1",3"-dioxolan-4"-yl)oximinomethyl)phenyl)oxymethylene]-4-(2-fluorophenyl)naptho[2,3-c]furan-1(3H)-one, O-methylE- and Z-(4"S)-7-[(3'-((2",2"-dimethyl-1",3"-dioxolan-4"-yl)oximinomethyl)phenyl)oxymethylene]-4-(2-chlorophenyl)naptho[2,3-c]furan-1-(3H)-one, O-methylE- and Z-(4"S)-7-[(3'-((2",2"-dimethyl-1",3"-dioxolan-4"-yl)oximinomethyl)phenyl)oxymethylene]-4-(3-methoxyphenyl)naptho[2,3-c]furan-1-(3H)-one, O-methylE- and Z-(4"S)-7-[(3'-((2",2"-dimethyl-1",3"-dioxolan-4"-yl)oximinomethyl)phenyl)oxymethylene]-4-(fur-2-yl)naptho[2,3-c]furan-1-(3H)-one, O-methylE- and Z-(4"S)-7-[(3'-((2",2"-dimethyl-1",3"-dioxolan-4"-yl)oximinomethyl)phenyl)oxymethylene]-4-(fur-3-yl)naptho[2,3-c]furan-1-(3H)-one, O-methylE- and Z-(4"S)-7-[(3'-((2",2"-dimethyl-1",3"-dioxolan-4"-yl)oximinomethyl)phenyl)oxymethylene]-4-(thien-3-yl)naptho[2,3-c]furan-1-(3H)-one, O-methylE- and Z-(4"S)-7-[(3'-((2",2"-dimethyl-1",3"-dioxolan-4"-yl)oximinomethyl)phenyl)oxymethylene]-4-(pyrid-3-yl)naptho[2,3-c]furan-1-(3H)-one, anti-(1"S,2"R)-7-[(5'-fluoro-3'-(1",2",3"-trimethoxyprop-1"-yl)phenyl)oxymethylene]-4-(4-fluorophenyl)-naptho[2,3-c]furan-1(3H)-one, anti-(1"S,2"R)-7-[(5'-fluoro-3'-(1",2",3"-trimethoxyprop-1"-yl)phenyl)oxymethylene]-4-phenylnaptho[2,3-c]furan-1(3H)-one, anti-(1"S,2"R)-7-[(5'-fluoro-3'-(1",2",3"-trimethoxyprop-1"-yl)phenyl)oxymethylene]-4-(4-chlorophenyl)-naptho[2,3-c]furan-1(3H)-one, anti-(1"S,2"R)-7-[(5'-fluoro-3'-(1",2",3"-trimethoxyprop-1"-yl)phenyl)oxymethylene]-4-(4-methoxyphenyl)naptho[2,3-c]furan-1(3H)-one, anti-(1"S,2"R)-7-[(5'-fluoro-3'-(1",2",3"-trimethoxyprop-1"-yl)phenyl)oxymethylene]-4-(2-fluorophenyl)-naptho[2,3-c]furan-1(3H)-one, anti-(1"S,2"R)-7-[(5'-fluoro-3'-(1",2",3"-trimethoxyprop-1"-yl)phenyl)oxymethylene]-4-(2-chlorophenyl)-naptho[2,3-c]furan-1(3H)-one, anti-(1"S,2"R)-7-[(5'-fluoro-3'-(1",2",3"-trimethoxyprop-1"-yl)phenyl)oxymethylene]-4-(3-methoxyphenyl)naptho[2,3-c]furan-1(3H)-one, anti-(1"S,2"R)-7-[(5'-fluoro-3'-(1",2",3"-trimethoxyprop-1"-yl)phenyl)oxymethylene]-4-(fur-2-yl)naptho[2,3-c]furan-1(3H)-one, anti-(1"S,2"R)-7-[(5'-fluoro-3'-(1",2",3"-trimethoxyprop-1"-yl)phenyl)oxymethylene]-4-(fur-3-yl)naptho[2,3-c]furan-1(3H)-one, anti-(1"S,2"R)-7-[(5'-fluoro-3'-(1",2",3"-trimethoxyprop-1"-yl)phenyl)oxymethylene]-4-(thien-3-yl)naptho[2,3-c]furan-1(3H)-one, anti-(1"S,2"R)-7-[(5'-fluoro-3'-(1",2",3"-trimethoxyprop-1"-yl)phenyl)oxymethylene]-4-(pyrid-3-yl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(4-fluorophenyl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-phenylnaptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(4-chlorophenyl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(4-methoxyphenyl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(2-fluorophenyl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(2-chlorophenyl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(3-methoxyphenyl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(fur-2-yl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(fur-3-yl)naptho[2,3-c]furan-1(3H)-one, (1"S )-O-methyl-E- and Z-7-[5'-fluoro-3'-((1",2"-dimethoxyeth-1-yl)oximinomethyl)phenyl)oxymethylene]-4-(thien-3-yl)naptho[2,3-c]furan-1(3H)-one, and (1"S )-O-methyl-E- and Z-7-[5'-fluoro-3'-((1",2"-dimethoxyeth-1-yl)oximinomethyl)phenyl)oxymethylene]-4-(pyrid-3-yl)naptho[2,3-c]furan-1(3H)-one, Preferred compounds are those in which Ar is selected from phenyl; phenyl substituted one or more groups selected from halogen, cyano, alkyl of one to four carbon atoms, haloalkyl of one to four carbon atoms, alkoxy of one to six carbon atoms, and alkoxycarbonyl where the alkyl portion is of one to four carbon atoms; furyl; furyl substituted with one or more groups selected from halogen, alkyl of one to four carbon atoms, and alkoxy of one to four carbon atoms; thienyl; and thienyl substituted with one or more groups selected from halogen, alkyl of one to four carbon atoms, and alkoxy of one to four carbon atoms.

The most preferred compounds are those in which Ar is phenyl or phenyl substituted one or more groups selected from halogen, cyano, alkyl of one to four carbon atoms, haloalkyl of one to four carbon atoms, alkoxy of one to six carbon atoms, and alkoxycarbonyl where the alkyl portion is of one to four carbon atoms.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23 187 challenge (final concentration of 8.3/μM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis in human whole blood. A representative result for a particular example is 52% at 13 nM for O-methyl-E- and Z-(4"S)-7-[(3'-((2",2"-dimethyl-1",3"-dioxolan-4"-yl)oximinomethyl)phenyl)oxymethylene]-4-(4-fluorophenyl)naptho[2,3-c]furan-1(3H)-one.

Pharmaceutical Compositions

The present invention also provides pharmaceutical compositions which comprise compounds of the present invention formulated together with one or more non-toxic pharmaceutically acceptable careers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monosteamte and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Solid dosage forms for oral administration include capsules, tablets, pills, powders, and granules. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonitc clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by money- or multilamellar hydrated liquid crystals that are dispersed in an aqueous medium. Any nontoxic, physiologically acceptable and metabolizable lipid capable of forming liposomes is can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed s preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) a0 that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the as compound at levels lower than required for to achieve the desired therapeutic effect and to gradually increase the dosage until the desired effect is achieved.

Generally dosage levels of about I to about 50, more preferably of about 5 to about 20 mg of active compound per kilogram of body weight per day are administered orally to a mammalian patient. If desired, the effective daily dose may 'be divided into multiple doses for purposes of administration, e.g. two to four separate doses per day.

Preparation of the Compounds of the Invention

The compounds of this invention may be prepared by a variety of synthetic routes. Representative procedures are outlined as follows. It should be understood that the groups Z, $R^1$, $R^2$, $R^4$, $R^5$, $R^6$, and $R^7$, as used herein, correspond to the groups identified above.

The preparation of compounds in which L is $>NOR^5$ is shown in Scheme 1. Bromobenzyl alcohol 1 is protected with a suitable acid-stable protecting group $P^1$. Suitable protecting groups may be found in Greene, Protective Groups in Organic Synthesis, 1981, John Wiley and Sons, Inc.. Representative protecting groups include t-butyl-dimethylsilyloxy and allyloxy. Protected alcohol 2 is then metallated using, for example, n-butyllithium in an organic solvent such as THF. Addition of glyceraldehyde acetonide to the aryllithium provides secondary alcohol 3, which is oxidized to ketone 4, for example using Swern oxidation conditions (Swern, D., Manusco, A. J., and Huang, S. L., J. Org. Chem., 1978, 43, 2480. Reaction of 4 with $HNOR^5$, affords oxime 5. Deprotection of the acetonide with mild acid, for example p-toluenesulfonic acid in methanol affords diol 6. Reaction of 6 with base, for example Nail and $R^1X$ or $R^2X$ where X is a suitable leaving group such as bromo, chloro, iodo, methanesulfonyl, trifluoromethanesulfonyl, or p-toluenesulfonyl provides dialkoxyl derivative 7. When $R^1$ and $R^2$ are different, the primary and secondary alcohols may be alkylated sequentially.

The dioxolane-containing oxime derivatives are prepared by condensation of diol 6 with ketone $R^6R^7CO$ under standard ketalization conditions. The representative compounds of the invention 9 and 10 are prepared by deprotection of 7 and 8, followed by coupling with the desired lactone under standard Mitsunobu conditions (triphenylphosphine, diethyl or diisopropylazodicarboxylate; see Mitsunobu, O., Synthesis, 1981, 1. The lactones are prepared as described in U.S. Pat. Nos. 5,227,399 and 5,252,599.

Scheme I

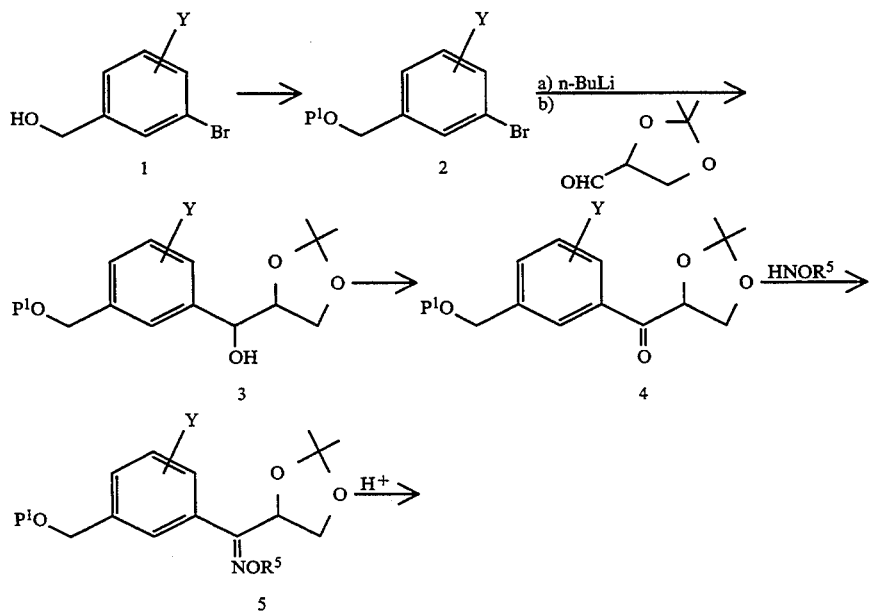

-continued
Scheme I

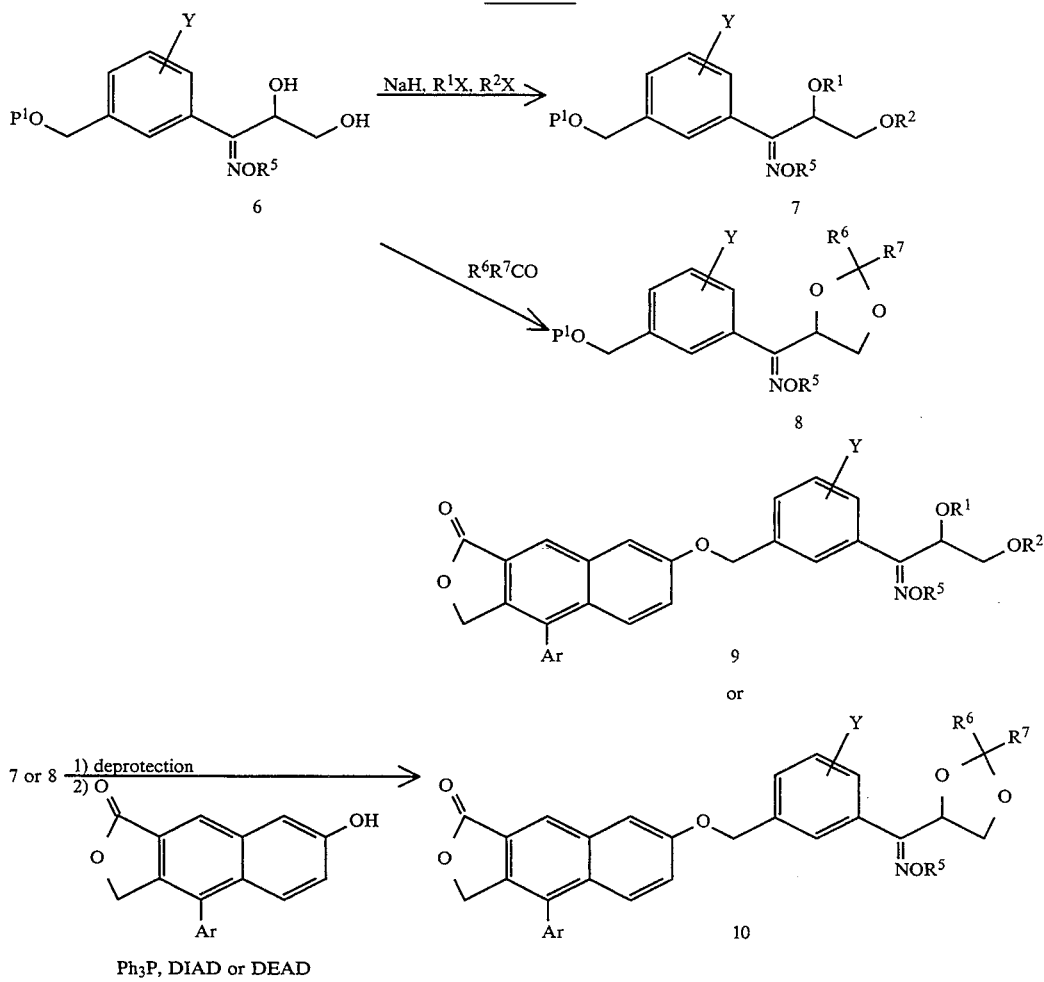

The preparation of the compounds of this invention in which L is $>C(R^3)OR^4$ is outlined in Scheme 2. Secondary alcohol 3, prepared as in Scheme 1, is alkylated by reaction with a base such as NaH and $R^4X$ where $R^4$ and X are defined above. The acetonide is then deprotected and diol 12 is reacted with base and $R^1X$ or $R^2X$ as described above to give the trialkoxyl intermediate 13. The dioxolane-containing intermediate 14 is prepared by condensation of 12 with $R^6R^7CO$ as described above. Representative compounds 15 and 16 are prepared by deprotection and Mitsunobu coupling of the benzyl alcohols with the desired lactones as described in Scheme 1. Compounds in which $R^3$ is alkyl are prepared by adding the corresponding Grignard reagent or organolithium reagent to ketone 4, followed by alkylation of the resulting alcohol and conversion to the desired compound as outlined below starting from alcohol 3.

Scheme 2

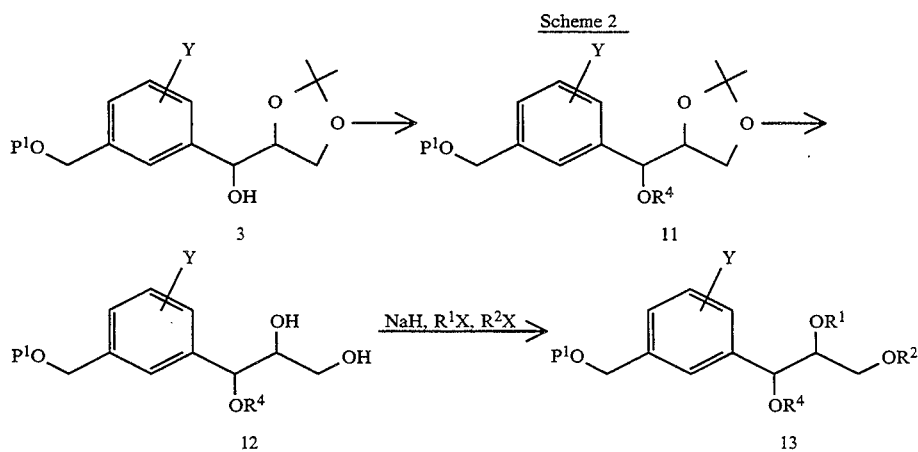

-continued
Scheme 2

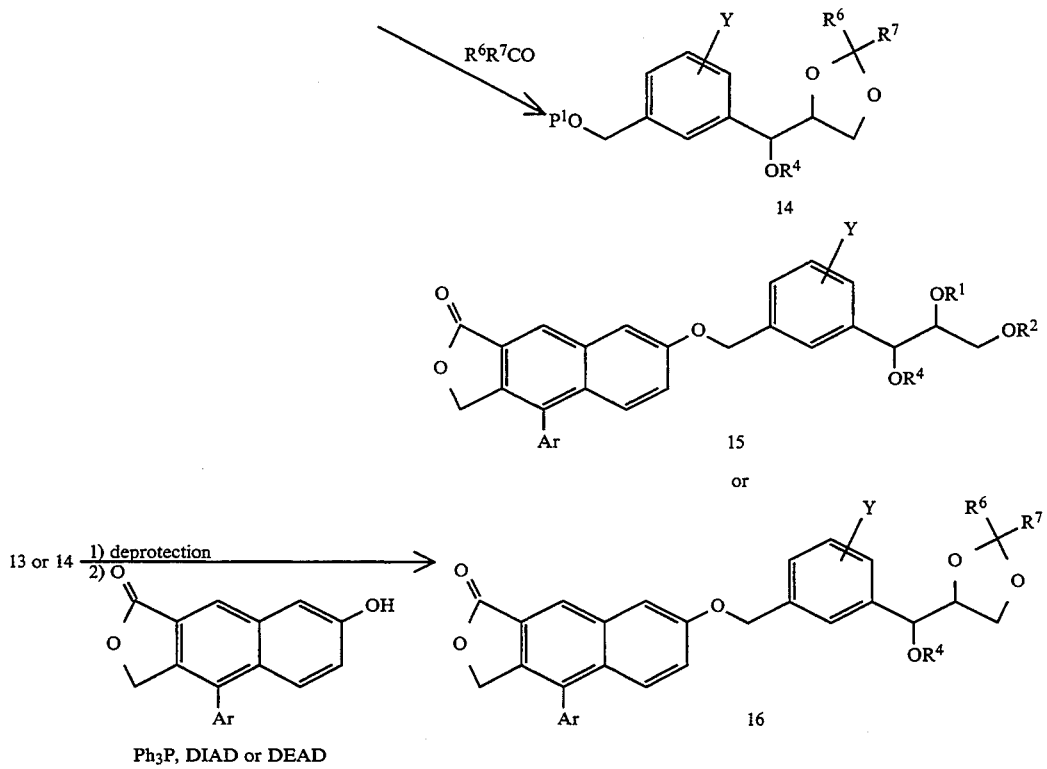

Ph₃P, DIAD or DEAD

The foregoing may be better understood by the following examples, which are presented for purposes of illustration and are not intended to limit the scope of the invention.

EXAMPLE 1

Preparation of O-methylE- and Z-(4"S)-7-[(3'-((2",2"-dimethyl-1",3"-dioxolan-4"-yl)oximinomethyl)-phenyl)oxymethylene]-4-(4-fluorophenyl)naptho[2,3-c]furan-1(3H)-one.

Step 1: 3-(t-butyldimethylsilyloxymethyl)bromobenzene.

To a solution of 3-bromobenzyl alcohol (5.00 g, 26.7 mmol) in freshly dried dimethylformamide (10 mL) was added t-butyldimethylsilyl chloride (5.13 g, 33 mmol) and imidazole (4.56 g, 67 mmol). The resulting solution was stirred overnight at ambient temperature. The reaction mixture was poured into water and extracted (3x, 50 mL 1:1 ether:hexanes). The combined organic layers were washed (2x, brine), dried over MgSO₄, filtered, and concentrated in vacuo to give a colorless oil which was passed through a short silica gel plug using 10% methylene chloride:hexanes to give pure 3-(t-butyldimethylsilyloxymethyl)bromobenzene (7.9 g, 98%). ¹H NMR (300 MHz, CDCl₃) δ 7.47 (1H, br s), 7.37 (1H, dt, J =7, 1 Hz), 7.16-7.25 (2H, m), 4.24 (2H, s), 0.94 (9H, s), 0.11 (6H, s). MS m/e 318/320(M+NH₄)⁺.

Step 2:. (4R)-4-((3'-(t-butyldimethylsilyloxymethyl)-phenyl)hydroxymethyl)-2,2-dimethyl-1,3-dioxolane.

To a -78° C. solution in freshly dried THF (100 mL) of 3-(t-butyldimethylsilyloxymethyl)bromobenzene (7.8 g, 25 mmol), prepared as in step 1, is was added n-butyl lithium (11.0 mL, 2.5M solution in hexanes, 27.5 mmol) via syringe. The reaction mixture was stirred for one hour at −78 ° C. and a solution of (R)-glyceraldehyde acetonide (3.58 g, 27.5 mmol, prepared as in Jackson, Synthetic Commun. 1988, 18(4), 337) in freshly dried THF (20 mL).was added. The resulting solution was stirred 30 min at −78 ° C., the cold bath was removed, and stirring was continued one hour. The reaction was quenched by adding excess saturated aqueous NH₄Cl. The reaction mixture was partitioned between saturated aqueous NH₄Cl and ethyl acetate. The combined organic layers were washed twice with brine, dried over MgSO₄, filtered, and concentrated in vacuo to give a colorless oil (8.44 g) which was purified by flash chromatography on silica gel (10%, then 15%, then 20% ethyl acetate/hexanes) to give (4R)-4-((3'-(t-butyldimethylsilyloxymethyl)phenyl)hydroxymethyl)-2,2-dimethyl-1,3-dioxolane (4.90 g, 55%) as a 1:1 mixture of diastereomers. ¹H NMR (300 MHz, CDCl₃) δ 7.23-7.37 (4H, m), 4.93 (0.5H, dd, J=3, 4 Hz), 4.72 (2H, s), 4.55 (0.5H, dd, J=3, 8 Hz),4.20-4.35 (1H, m), 3.98 (0.5H, dd, J=6, 9 Hz), 3.68-3.83 (1.5H, m), 2.76 (0.5H, d, J=3 Hz), 2.42 (0.5H, d, J=2.5 Hz), 1.52 (3H, s), 1.48 (3H, s), 1.38 (3H, s), 1.36 (3H, s), 0.94 (9H, s), 0.11 (6H, s). MS m/e 352 (M)⁺, 370 (M+NH₄)⁺.

Step 3: (4R)-4-((3'-(t-butyldimethylsilyloxymethyl)-phenyl)oxomethyl)-2,2-dimethyl-1,3-dioxolane.

Following the Swern oxidation procedure (Swern, D.; Manusco, A. J.; Huang, S. L., J. Org. Chem. 1978, 43, 2480) the 1:1 diastereomeric mixture of (4R)-4-((3'-(t-butyldimethylsilyloxymethyl)phenyl)hydroxymethyl)-2,2-dimethyl-1,3-dioxolane (4.90 g, 13.9 mmol), prepared in step 2, was oxidized to the corresponding ketone. Purification by flash chromatography (5% ethyl acetate hexanes) provided (4R)-4-((3'-(t-butyldimethylsilyloxymethyl)phenyl)oxomethyl)-2,2-dimethyl-1,3-dioxolane (3.08 g, 63%). ¹H NMR (300 MHz, CDCl₃) δ 7.97 (1H, br s), 7.88 (1H, dr, J=8, 1 Hz), 7.56 (1H, dt, J=8, 1 Hz), 7.44 (1H, t, J=8, 8 Hz), 5.29 (1H, dd, J=6, 7.5 Hz), 4.79 (2H, s), 4.34 (1H, dd, J=9, 7.5 Hz), 4.25 (1H, dd, J=9, 6 Hz), 1.49 (3H, s), 1.44 (3H, s), 0.96 (9H, s), 0.12 (6H, s). MS m/e 351 (M+H)+, 368 (M+NH4)+.

Step 4: E- and Z -O-methyl-(4R)-4-((3-(t-butyldimethylsilyoxymethyl)phenyl)oximinomethyl)-1,3-dioxolane.

A solution in absolute ethanol (38 mL) of (4R)-4-((3'-(t-butyldimethylsilyloxymethyl)phenyl)oxomethyl)-2,2-dimethyl-1,3-dioxolane (2.60 g, 7.42 mmol), prepared as in step 3, methoxylamine hydrochloride (1.24 g, 14.8 mmol), and pyridine (1.6 mL, 18.5 mmol) was stirred at ambient temperature for one hour and then concentrated in vacuo. The residue was partitioned between 3% aqueous HCl and ethyl acetate. The organic layer was washed once with saturated aqueous NaHCO3, twice with brine, dried over MgSO4, filtered, and concentrated in vacuo to give E- and Z-O-methyl-(4R)-4-((3'-(t-butyldimethylsilyloxymethyl)phenyl)oximinomethyl)-2,2-dimethyl-1,3-dioxolane as a colorless oil (2.96 g) estimated to be a 2:1 mixture of geometrical isomers, which was carded on without further purification. $^1$H NMR (300 MHz, CDCl$_3$) δ 7.25–7.48 (4H, m), 5.47 (0.66H, t, J=7 Hz), 4.89 (0.33H, dd, J=6.5, 7 Hz), 4.75 (2H, s), 4.45 (0.66H, dd, J=8, 9 Hz), 4.13 (1H, dd, J=9, 6.5 Hz), 3.96 (0.66(3H), s), 3.83 (0.33(3H), s), 3.84–3.93 (1H, m), 1.39 (0.33(3H), s), 1.37 (0.66(3H), s), 1.29 (0.33(3H), s), 1.24 (0.66(3H), s), 0.93 (9H, s), 0.10 (6H, s). MS m/e 380 (M+H)+, 397 (M+NH4)+.

Step 5: E- and Z -O-methyl-(4R)-4-((3'-(hydroxymethyl)phenyl)oximinomethyl)-2,2-dimethyl-1,3-dioxolane.

To a solution in dry THF (40 mL) of E- and Z-O-methyl-(4R)-4-((3'-(t-butyldimethylsilyloxymethyl)phenyl)oximinomethyl)-2,2-dimethyl-1,3-dioxolane (2.96 g, ~95% pure, 7.4 mmol), prepared as in step 4, was added tetra-n-butylammonium fluoride (1M in H$_2$O, 20 mL, 20 mmol). The reaction was stirred for one hour at ambient temperature and partitioned between ethyl acetate and water. The organic layer was washed once with water, twice with brine, dried over MgSO$_4$, filtered, and concentrated in vacuo to give a colorless oil (3.19 g). Purification by chromatography on silica gel (CH$_2$Cl$_2$, then 10% ethyl acetate:CH$_2$Cl2) gave E- and Z-O-methyl-(4R)-4-((3'-(hydroxymethyl)phenyl)oximinomethyl)-2,2-dimethyl-1,3-dioxolane (1.03 g, 52%) as a colorless oil. The alcohol was a 2:1 ratio of E- and Z- isomers. $^1$H NMR (300 MHz, D$_6$-DMSO) δ 7.20–7.48 (4H, m), 5.48 (0.66H, d,d; J=8, 7 Hz), 5.28 (0.33H, t, J=6, 6 Hz), 5.26 (0.66H, t, J=6, 6 Hz), 4.93 (0.33H, t, .J=6.5, 6.5 Hz), 4.54 (2H, d, J=6 Hz), 4.42 (0.66H, d,d, J=7.5, 8 Hz), 4.16 (0.33H, dd, J=9, 6.5 Hz), 3.93 (0.66(3H), s), 3.70–3.83 (1H, m), 3.69 (0.33(3H), s), 1.33 (3H, br s), 1.24 (0.66(3H), s), 1.19 (0.33(3H), s). MS m/e 266 (M+H)+, 283 (M+NH4)+.

Step 6: O-methylE- and Z-(4"S)-7-[(3'-((2",2"-dimethyl-1",3"-dioxolan-4"-yl)oximinomeyl)phenyl)oxymethylene]-4-(4-fluorophenyl)naptho[2,3-c]furan-1(3H)-one.

To a 0° C. solution in dry THF(65 mL) of E- and Z-O-methyl-(4R)-4-((3'-(hydroxymethyl)phenyl)oximinomethyl)-2,2-dimethyl-1,3-dioxolane (1.03 g, 3.88 mmol), prepared as in step 5, 7-hydroxy-4-(4-fluorophenyl)naptho[2,3-c]furan-1(3H)-one (1.18 g, 4.00 mmol), prepared as described in US Pat. No. 5,227,399, and triphenylphosphine (1.32 g, 5.00 mmol) was added diisopropylazodicarboxylate (1.01 g, 5.00 mmol) in dry THF (10 mL). The cold bath was removed and the reaction mixture stirred for two hours at ambient temperature. The volatiles were removed in vacuo and the resulting slurry was dissolved in ether (~35 mL), diluted with hexanes (~13 mL), and cooled to −20° C. overnight. The supernatant was decanted from the solid and concentrated in vacuo to provide a residue (3.16 g) which was purified by chromatography on silica gel (CH$_2$Cl$_2$, then 0.5% ethyl acetate:hexanes) to provide products in the following order of elution: Z-isomer (560 as mg, 27%), E- and Z-isomers (299 mg, 14%), E-isomer (186 mg, 9%) all as foamy solids. Z-isomer: $^1$HNMR (300 MHz, CDCl$_3$) δ 8.38 (1H, s), 7.66–7.71 (2H, m), 7.46–7.57 (2H, m), 7.22–7.44 (7H, m), 5.50 (1H, t, J=7.5 Hz), 5.23 (2H, s), 4.47 (1H, t, J=8, 8 Hz), 3.97 (3H, s), 3.89 (1H, d,d, J=6.5, 8.5 Hz), 1.37 (3H, s), 1.24 (3H, s). MS m/e 559 (M+NH4)+. Analysis calc'd for C$_{32}$H$_{28}$N$_6$F(0.25 H$_2$O): C, 70.38; H, 5.26; N, 2.56. Found: C, 70.28; H, 5.16; N, 2.47. E-isomer: $^1$H NMR (300 MHz, CDCl$_3$) δ 8.38 (1H; s), 7.66–7.71 (2H, m), 7.48–7.57: (2H, m), 7.22–7.44 (7H, m), 5.24 (4H, s), 4.92 (1H, t, J=7.5 Hz), 4.23 (1H, d,d, J 9, 7 Hz), 3.93 (1H, d,d, J=6.5, 5.5 Hz), 3.86 (3H, s), 1.39 (3H, s), 1.27 (3H, s). MS m/e 559 (M+NH4)+. Analysis calc'd for C$_{32}$H$_{28}$NO$_6$F: C, 70.97; H, 5.21; N, 2.59. Found: C, 70.80; H, 5.23; N, 2.65.

EXAMPLE 2 anti-(1"S,2"R)-7-[(5'-fluoro-3'-(1",2",3"-trimethoxyprop-1"-yl)phenyl)oxymethylene]-4-(4-fluorophenyl)-naptho[2,3-c]furan-1(3H)-one.

Step 1: 5-fluoro-3-hydroxymethylbromobenzene.

The desired compound was prepared by reaction of 5-fluoro-3-hydroxybromobenzene with trifluoromethanesulfonic anhydride and pyridine, followed by reaction of the resulting triflate with 1,1-bis(diphenylphosphino)ferrocene, Pd(II)acetate, and CO as described in U.S. Pat. No. 5,227,399, Example 2, steps 1 and 2.

Step 2: 5-fluoro-3-(allyloxymethyl)bromobenzene.

The desired compound is prepared according to the method of Example 2, step 1, except substituting 5-fluoro-3-hydroxybromobenzene for 3-hydroxybromobenzene.

Step 3: (4R, 1'R)- and (4R, 1'S)-2,2-dimethyl-4-[(5-fluoro-3-(allyloxymethyl)phenyl)hydroxymethyl-1,3-dioxolane.

The desired compound is prepared according to the method of Example 1, step 2, except substituting 5-fluoro-3-(allyloxmethyl)bromobenzene, prepared as in step 2, for 3-(t-butyldimethylsilyloxymethyl)bromobenzene.

Step 4: syn-(4R, 1'R)- and anti-(4R, 1'S)-2,2-dimethyl-4-[(5-fluoro-3(allyloxymethyl)phenyl)methyloxymethyl]- 1,3-dioxolane.

The desired compound is prepared by reaction of a solution in DMF of (4R, 1'R)- and (4R, 1'S)-2,2-dimethyl-4-[(3-(allyloxymethyl)phenyl)hydroxymethyl]-1,3-dioxolane, prepared as in step 3, with NaH and methyl iodide.

Step 5: anti-(1S, 2R)-2,3-dihydroxy-1-[(5-fluoro-3-(allyloxymethyl)phenyl)]-1-methoxypropane.

The desired compound is prepared by hydrolysis of anti-(4R, 1'S)-2,2-dimethyl-4-[(5-fluoro-3-(allyloxymethyl)phenyl)methyloxymethyl]-1,3-dioxolane, prepared as in step 2, using p-toluenesulfonic acid in methanol.

Step 6: anti-(1S, 2R)- 1-[(5-fluoro-3-(allyloxymethyl)phenyl)]- 1,2,3-trimethoxypropane.

The desired compound is prepared by reaction of a solution in THF of anti-(1S, 2R)-2,3-dihydroxy-1-[(3-(allyloxymethyl)phenyl)]-1-methoxypropane, prepared as in step 5, with 2 equivalents of NaH and methyl iodide.

Step 7: anti-(1S,2R)-1-[(5-fluoro-3-hydroxymethylphenyl)]- 1,2,3-trimethoxypropane.

The desired compound is prepared by removal of the allyl protecting group from anti-(1S, 2R)-1-[(5-fluoro-3-(allyloxymethyl)phenyl) ]- 1,2,3-trimethoxypropane, prepared as in step 6, using PdCl2, aqueous DMF, CuCl, and O2 according to the method of Mereyala, H. B., and Guntha, S. Tetrahedron Lett., 1993, 34(43), 6929.

Step 8: anti-(1″S,2″R)-7-[(5′-fluoro-3′-(1″,2″,3″-trimethoxyprop-1″-yl)phenyl)oxymethylene]-4-(4-fluorophenyl)naptho[2,3-c]furan-1(3H)-one.

The desired compound is prepared according to the method of Example 1, step 6, except substituting anti-(1S,2R)- 1-[(5-fluoro-3-hydroxyphen-1-yl)]-1,2,3-trimethoxypropane, prepared as in step 7, for E- and Z- O-methyl-(4R)-4-((3-(hydroxymethyl)phenyl) oximinomethyl)-1,3-dioxolane.

EXAMPLE 3

Preparation of (1″S)-O-methyl-E- and Z-7-[5′-fluoro-3′-((1″,2″-dimethoxyeth-1-yl)oximinomethyl)phenyl)oxymethylene]-4-(4-fluorophenyl)naptho[2,3-c]furan-1(3H)-one.

Step 1: (4S)-4-((5′-fluoro-3′-(alloxymethyl)phenyl)oximinomethyl)-2,2-dimethyl-1,3-dioxolane.

The desired compound is prepared according to the method of Example 1, steps 2-4, except substituting 5-fluoro-3-(allyloxymethyl)bromobenzene, prepared as in Example 2, step 2, for 3-(t-butyldimethylsilyloxymethyl)bromobenzene.

Step 2: (4S)-1-((5′-fluoro-3′-(allyloxymethyl)phenyl)oximinomethyl)-1,2-dimethoxyethane.

The desired compound is prepared according to the method of Example 2, steps 5 and 6, except substituting (4S)-4-((5′-fluoro-3′-(alloxymethyl)phenyl)oximinomethyl)-2,2-dimethyl-1,3-dioxolane, prepared as in step 1, for anti-(4R, 1′S)-2,2-dimethyl-4-[(5-fluoro-3-(allyloxymethyl)phenyl)methyloxymethyl]-1,3-dioxolane.

Step 3: (4S)-1-((5′-fluoro-3′-hydroxymethylphenyl)oximinomethyl)-1,2-dimethoxyethane.

The desired compound is prepared by reaction of (4S)-1-((5′-fluoro-3′-(allyloxymethyl)phenyl)oximinomethyl)-1,2-dimethoxyethane, prepared as in step 2, with Pd(NH3)2Cl2 in t-BuOH according to the method of Bieg, T., and Szeja, W., J. Carbohydr. Chem., 1985, 4(3), 441.

Step 4: (1″S)-O-methyl-E- and Z-7-[5′-fluoro-3′-((1″,2″-dimethoxyeth-1-yl)oximinomethyl)phenyl)oxymethylene]-4-(4-fluorophenyl)naptho[2,3-c]furan-1(3H)-one.

The desired compound is prepared according to the method of Example 1, step 6, except substituting (4S)-1-((5′-fluoro-3′-hydroxymethylphenyl)oximinomethyl)-1,2-dimethoxyethane, prepared as in step 5, for E- and Z- O-methyl-(4R)-4-((3′-(hydroxymethyl)phenyl)oximinomethyl)-2,2-dimethyl-1,3-dioxolane.

The compounds shown in Table 1 are prepared according to the method of Example 1, except substituting the desired 7-hydroxy-4-(aryl)naptho[2,3-c]furan-1(3H)-one, prepared as described in U.S. Pat. No. 5,227,399, or 7-hydroxy-4-(heteroaryl)naptho[2,3-c]furan-1(3H)-one, prepared as described in U.S. Pat. No. 5,252,599 for 7-hydroxy-4-(4-fluorophenyl)naptho[2,3-c]furan-1(3H)-one.

TABLE 1

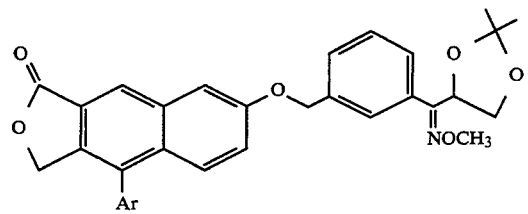

| Example | Ar |
| --- | --- |
| 4 | phenyl |
| 5 | 4-chlorophenyl |
| 6 | 4-methoxyphenyl |
| 7 | 2-fluorophenyl |
| 8 | 2-chlorophenyl |
| 9 | 3-methoxyphenyl |
| 10 | 2-furyl |
| 11 | 3-furyl |
| 12 | 3-thienyl |
| 13 | 3-pyridyl |

The compounds shown in Table 2 are prepared according to the method of Example 2, except substituting the desired 7-hydroxy-4-(aryl)naptho[2,3-c]furan-1(3H)-one, prepared as described in U.S. Pat. No. 5,227,399, or 7-hydroxy-4-(heteroaryl)naptho[2,3-c]furan-1(3H)-one, prepared as described in U.S. Pat. No. 5,252,599 for 7-hydroxy-4-(4-fluorophenyl)naptho[2,3-c]furan-1(3H)-one.

TABLE 2

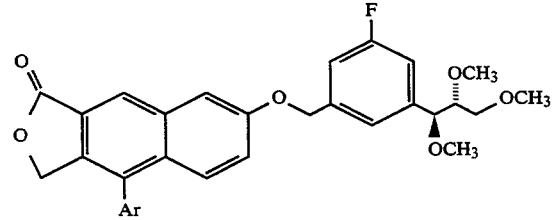

| Example | Ar |
| --- | --- |
| 14 | phenyl |
| 15 | 4-chlorophenyl |
| 16 | 4-methoxyphenyl |
| 17 | 2-fluorophenyl |
| 18 | 2-chlorophenyl |
| 19 | 3-methoxyphenyl |
| 20 | 2-furyl |
| 21 | 3-furyl |
| 22 | 3-thienyl |
| 23 | 3-pyridyl |

The compounds shown in Table 3 are prepared according to the method of Example 3, except substituting the desired 7-hydroxy-4-(aryl)naptho[23-c]furan-1(3H)-one, prepared as described in U.S. Pat. No. 5,227,399, or 7-hydroxy-4-(heteroaryl)naptho[2,3-c]furan-1(3H)-one, prepared as described in U.S. Pat. No. 5,252,599 for 7-hydroxy-4-(4-fluorophenyl)naptho[2,3-c]furan-1(3H)-one.

TABLE 3

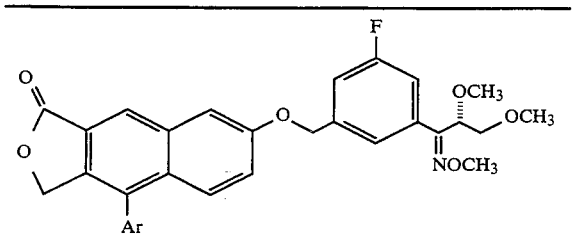

| Example | Ar |
| --- | --- |
| 24 | phenyl |
| 25 | 4-chlorophenyl |
| 26 | 4-methoxyphenyl |
| 27 | 2-fluorophenyl |
| 28 | 2-chlorophenyl |
| 29 | 3-methoxyphenyl |
| 30 | 2-furyl |
| 31 | 3-furyl |
| 32 | 3-thienyl |
| 33 | 3-pyridyl |

Specific salts of compounds of the present invention are exemplified by Examples 34–36 below.

EXAMPLE 34

Preparation of O-methylE- and Z-(4″S)-3-hydroxymethyl-4-(4-fluorophenyl)-7-[(3′-((2″,2″-dimethyl-1″,3″-dioxolan-4″-yl)oximinomethyl)-phenyl)oxymethylene]-2-naphthoic acid, sodium salt.

The sodium salt is prepared by heating a mixture in dioxane of O-methylE- and Z-(4″S)-7-[(3′-((2″,2″-dimethyl-1″,3″-dioxolan-4″-yl)oximinomethyl)phenyl)oxymethylene]-4-(4-fluorophenyl)naptho[2,3-c]furan-1(3H)-one, prepared as in Example 1, and aqueous 1N NaOH (1 equiv.) for an amount of time sufficient to consume substantially all of the starting lactone, followed by evaporation to dryness.

EXAMPLE 35

Preparation of anti-(1″S,2″R)-3-hydroxymethyl-4-(4-fluorophenyl)-7-[(5′-fluoro-3′-(1″,2″,3″-trimethoxyprop-1″-yl)phenyl)oxymethylene]-2-naphthoic acid, sodium salt.

The desired compound is prepared by treating anti-(1″S,2″R)-7-[(5′-fluoro-3′-(1″,2″,3″-trimethoxyprop-1″-yl)phenyl)oxymethylene]-4-(4-fluorophenyl)naptho[2,3-c]furan-1(3H)-one, prepared as in Example 2, with aqueous NaOH as described in Example 34.

EXAMPLE 36

Preparation of (1″S)-O-methyl-E- and Z-3-hydroxymethyl-4-(4-fluorophenyl)-7-[5′-fluoro-3′-((1″,2″-dimethoxyeth-1-yl)oximinomethyl)phenyl)oxymethylene]-2-naphthoic acid, sodium salt.

The desired compound is prepared by treating (1″S)-O-methyl-E- and Z-7-[5′-fluoro-3′-((1″,2″-dimethoxyeth-1-yl)oximinomethyl)phenyl)oxymethylene]-4-(4-fluorophenyl)naptho2,3-c]furan-1(3H)-one, prepared as in Example 3, with aqueous NaOH as described in Example 34.

We claim:

1. A compound or pharmaceutically acceptable salt thereof of formula

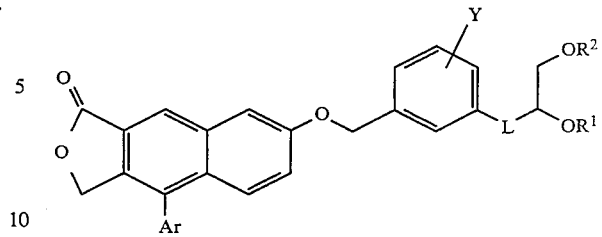

wherein
Ar is selected from the group consisting of
  unsubstituted phenyl,
  phenyl substituted one or more groups selected from
    halogen,
    cyano,
    alkyl of one to four carbon atoms,
    haloalkyl of one to four carbon atoms,
    alkoxy of one to six carbon atoms, and
    alkoxycarbonyl wherein the alkyl portion is of one to four carbon atoms,
  unsubstituted furyl,
  furyl substituted with one or more groups selected from
    halogen,
    alkyl of one to four carbon atoms, and
    alkoxy of one to four carbon atoms,
  unsubstituted pyridyl,
  pyridyl substituted with one or more groups selected from
    halogen,
    alkyl of one to four carbon atoms, and
    alkoxy of one to four carbon atoms,
  unsubstituted thienyl, and
  thienyl substituted with one or more groups selected from
    halogen,
    alkyl of one to four carbon atoms, and
    alkoxy of one to four carbon atoms;
Y is selected from the group consisting of
  hydrogen,
  halogen,
  cyano,
  alkyl of one to four carbon atoms,
  haloalkyl of one to four carbon atoms,
  alkoxy of one to six carbon atoms, and
  alkoxycarbonyl wherein the alkyl portion is of one to four carbon atoms;
L is selected from the group consisting of
  (a)

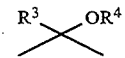

wherein $R^3$ is hydrogen or alkyl of one to four carbon atoms, and $R^4$ is alkyl of one to four carbon atoms, and
  (b)

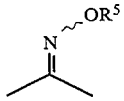

wherein R⁵ is hydrogen or alkyl of one to four carbon atoms; and

R¹ and R² are independently alkyl of one to four carbon atoms, or taken together with the oxygen atoms to which they are attached define a group of the formula

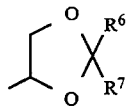

wherein R⁶ and R⁷ are independently selected from the group consisting of
hydrogen,
alkyl of one to four carbon atoms,
alkoxy of one to four carbon atoms, and
haloalkyl of one to four carbon atoms, and
the free valence bond is attached to L.

2. A compound as defined by claim 1, or a pharmaceutically acceptable salt thereof wherein Ar is selected from the group consisting of
unsubstituted furyl,
furyl substituted with one or more groups selected from
halogen,
alkyl of one to four carbon atoms, and
alkoxy of one to four carbon atoms,
unsubstituted thienyl, and
thienyl substituted with one or more groups selected from
halogen,
alkyl of one to four carbon atoms, and
alkoxy of one to four carbon atoms.

3. A compound as defined by claim 2, or a pharmaceutically acceptable salt thereof wherein L is

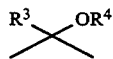

wherein R³ is hydrogen or alkyl of one to four carbon atoms, and R⁴ is alkyl of one to four carbon atoms.

4. A compound as defined by claim 2, or a pharmaceutically acceptable salt thereof wherein L is

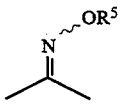

wherein R⁵ is hydrogen or alkyl of one to four carbon atoms.

5. A compound as defined by claim 1, or a pharmaceutically acceptable salt thereof wherein Ar is
unsubstituted phenyl, or
phenyl substituted one or more groups selected from
halogen,
cyano,
alkyl of one to four carbon atoms,
haloalkyl of one to four carbon atoms,
alkoxy of one to six carbon atoms, and
alkoxycarbonyl wherein the alkyl portion is of one to four carbon atoms.

6. A compound as defined by claim 5, or a pharmaceutically acceptable salt thereof wherein L is

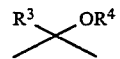

wherein R³ is hydrogen or alkyl of one to four carbon atoms, and R⁴ is alkyl of one to four carbon atoms.

7. A compound as defined by claim 5, or a pharmaceutically acceptable salt thereof wherein L is

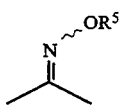

wherein R⁵ is hydrogen or alkyl of one to four carbon atoms.

8. A compound selected from the group consisting of
O-methyl-E-(4″S)-7-[(3′-((2″,2″-dimethyl-1″,3″-dioxolan-4″-yl)oximinomethyl)phenyl)oxymethylene]-4-(4-fluorophenyl)naptho[2,3-c]furan-1(3H)-one, and
O-methyl-Z-(4″S)-7-[(3″-((2″,2″-dimethyl-1″,3″-dioxolan-4″-yl)oximinomethyl)phenyl)oxymethylene]-4-(4-fluorophenyl)naptho[2,3-c]furan-1(3H)-one,
or a pharmaceutically acceptable salt thereof.

9. A compound selected from the group consisting of
O-methyl-E-(4″S)-3-hydroxymethyl-4-(4-fluorophenyl)-7-[(3′-((2″,2″-dimethyl-1″,3″-dioxolan-4″-yl)oximinomethyl)phenyl)oxymethylene]-2-naphthoic acid, sodium salt;
O-methyl-Z-(4″S)-3-hydroxymethyl-4-(4-fluorophenyl)-7-[(3′-((2″,2″-dimethyl-1″,3″-dioxolan-4″-yl)oximinomethyl)phenyl)oxymethylene]-2-naphthoic acid, sodium salt;
anti-(1″S,2″R)-3-hydroxymethyl-4-(4-fluorophenyl)-7-[(5′-fluoro-3′-(1″,2″,3″-trimethoxyprop-1″-yl)phenyl)oxymethylene]-2-naphthoic acid, sodium salt;
(1″S)-O-methyl-E-3-hydroxymethyl-4-(4-fluorophenyl)-7-[5′-fluoro-3′-((1″,2″-dimethoxyeth-1-yl)oximinomethyl)phenyl)oxymethylene]-2-naphthoic acid, sodium salt; and
Z-3-hydroxymethyl-4-(4-fluorophenyl)-7-[5′-fluoro-3′-((1″,2″-dimethoxyeth-1-yl)oximinomethyl)phenyl)oxymethylene]-2-naphthoic acid, sodium salt.

10. A pharmaceutical composition for inhibiting the biosynthesis of leukotrienes in a host animal comprising a therapeutically effective amount of a compound as defined by claim 1 in combination with a pharmaceutically acceptable carrier.

11. A method of inhibiting the biosynthesis of leukotrienes comprising administering to a mammal in need of such treatment a therapeutically effective amount of a compound as defined by claim 1.

* * * * *